United States Patent
Laviola et al.

(10) Patent No.: US 10,578,686 B2
(45) Date of Patent: Mar. 3, 2020

(54) SYSTEM AND METHOD FOR MRI LOCAL COIL DESIGN

(71) Applicant: INVIVO CORPORATION, Andover, MA (US)

(72) Inventors: John Laviola, Orange, CT (US); Thomas DeYoung, Hopewell Junction, NY (US); Raymond Ruthenberg, Toronto (CA)

(73) Assignee: Invivo Corporation, Andover, MA (US)

( * ) Notice: Subject to any disclaimer, the term of this patent is extended or adjusted under 35 U.S.C. 154(b) by 1194 days.

(21) Appl. No.: 14/375,595

(22) PCT Filed: Feb. 1, 2013

(86) PCT No.: PCT/US2013/024250
§ 371 (c)(1),
(2) Date: Jul. 30, 2014

(87) PCT Pub. No.: WO2013/116583
PCT Pub. Date: Aug. 8, 2013

(65) Prior Publication Data
US 2015/0005619 A1    Jan. 1, 2015

Related U.S. Application Data

(60) Provisional application No. 61/593,522, filed on Feb. 1, 2012.

(51) Int. Cl.
*G01R 33/341* (2006.01)
*G01R 33/34* (2006.01)
(Continued)

(52) U.S. Cl.
CPC ............ *G01R 33/341* (2013.01); *A61B 5/004* (2013.01); *A61B 5/055* (2013.01); *A61B 5/4312* (2013.01);
(Continued)

(58) Field of Classification Search
CPC .............. G01R 33/34; G01R 33/34007; G01R 33/34046–34076; G01R 33/341–3415
See application file for complete search history.

(56) References Cited

U.S. PATENT DOCUMENTS 5,214,403 A * 5/1993 Bogaerts ............. H01F 27/2804
336/200
5,363,845 A * 11/1994 Chowdhury ......... A61B 5/0555
324/318

(Continued)

OTHER PUBLICATIONS

"Molex Produces 20 Millionth Antenna with LDS Technology." Medical Devices & Surgical Technology Week. NewsRX. 2009. HighBeam Research. Nov. 14, 2016 <https://www.highbeam.com>.*

(Continued)

*Primary Examiner* — Angela M Hoffa

(57) ABSTRACT

An MRI local coil system for use with an MRI scanner to image a breast, the system comprising a plastic housing and an RF coil system. The RF coil system comprises a conductor and electronics. The electronics comprises a capacitor and a blocking circuit. The conductor and the electronics are disposed within the plastic housing and the conductor is integrally formed with the plastic housing.

16 Claims, 4 Drawing Sheets

(51) Int. Cl.
 *B29C 64/153* (2017.01)
 *A61B 5/00* (2006.01)
 *A61B 5/055* (2006.01)
 *B29C 45/14* (2006.01)
 *B29L 31/34* (2006.01)

(52) U.S. Cl.
 CPC ............ *B29C 45/14* (2013.01); *B29C 64/153* (2017.08); *G01R 33/34007* (2013.01); *B29L 2031/3481* (2013.01)

(56) References Cited

U.S. PATENT DOCUMENTS

| | | | | |
|---|---|---|---|---|
| 5,457,387 | A | | 10/1995 | Patrick |
| 5,755,667 | A | * | 5/1998 | Friedrich ......... G01R 33/34084 324/318 |
| 6,441,612 | B1 | * | 8/2002 | Shimo .............. G01R 33/34053 324/307 |
| 7,970,452 | B2 | | 6/2011 | Piron et al. |
| 2008/0077005 | A1 | * | 3/2008 | Piron .................. A61B 5/0555 600/411 |
| 2008/0129295 | A1 | * | 6/2008 | Carlton ................ G01R 33/341 324/318 |
| 2008/0174314 | A1 | | 7/2008 | Holwell et al. |
| 2008/0275333 | A1 | | 11/2008 | Fain et al. |
| 2008/0306377 | A1 | | 12/2008 | Piron |
| 2009/0124889 | A1 | * | 5/2009 | Guan .................. G01R 33/341 600/422 |
| 2009/0292051 | A1 | | 11/2009 | Li |

OTHER PUBLICATIONS

PCT/US13/24250, International Search Report dated May 7, 2013.

Insko et al "Multicoil Array for High Resolution Imaging of the Breast" Magnetic Resonance in Medicine vol. 37, No. 5, May 1, 1997, p. 778-784.

* cited by examiner

SYSTEM AND METHOD FOR MRI LOCAL COIL DESIGN

CROSS REFERENCE TO RELATED APPLICATION(S)

This application is a National Phase entry under 35 U.S.C. § 371 of International Patent Application No. PCT/US2013/024250, having an international filing date of Feb. 1, 2013, which claims priority to and the benefit of U.S. Provisional Patent Application No. 61/593,522, filed on Feb. 12 012, the entirety of which is incorporated herein by reference.

FIELD OF THE INVENTION

This application generally relates to medical imaging and more specifically to a system and method for an MRI local coil design.

BACKGROUND OF THE INVENTION

Magnetic resonance imaging (MRI) detects the faint nuclear magnetic resonance (NMR) signals given off by protons in the presence of a strong magnetic field after excitation by a radio frequency signal. The NMR signals are detected using antennae termed "coils". The term "coil" is also commonly used to refer to the antenna(e) and its housing or support structure. Thus "coil" may refer to a structure that contains a number of coils. "Coil element(s)" is used to refer to the electrical part of the device, the radio frequency coil or antennae.

NMR signals are extremely faint. Sensitivity of a coil to these signals decreases rapidly with increasing distance between the coil and the volume of interest. Coils are therefore placed in close proximity to the region of interest of the imaged object. The size of the local coils is kept small to allow them to be easily fit to the patient on the MRI patient table and to enable imaging of only the imaging volume of interest, since imaging regions that are not required adds noise to the acquired signal unnecessarily. Coils local to the anatomy of interest tend to have a higher signal-to-noise ratio (SNR) than larger coils such as a "body coil" which is useful for obtaining large survey scans of the patient.

Use of MRI to distinguish pathologic tissue from healthy tissue has proven advantageous in some respects in comparison to other imaging modalities. For example, MRI uses non-ionizing radio frequency (RF) signals to acquire images, in contrast to the use of ionizing radiation used with computed tomography scanners. Moreover, MRI has shown improved sensitivity in comparison to other imaging modalities.

Various limitations, however, have impeded widespread adoption of the use of MRI for imaging portions of the body despite its advantages. One impediment is the cost of MRI equipment. MRI scanners are expensive. Body coils present numerous complexities and issues so local coils have developed to isolate regions of the body of interest, but MRI local coils also have cost concerns. Nonlimiting examples of MRI local coils include U.S. Pat. Nos. 7,379,769 and 7,970,452, commonly owned by the assignee for the present invention. For example, the housing of a local coil constrains resources. In addition, local coil designs often include multiple components that are complicated to assemble. The complicated assembly can affect precision and repeatability of assembly.

What is needed, then, is a MRI local coil design with fewer parts and repeatable assembly. The MRI local coil design is preferably cost-effective, reliable, easier and/or faster to manufacture, and/or easier and/or faster to assemble with more precision.

SUMMARY OF THE INVENTION

In an aspect of the invention, an MRI local coil system for use with an MRI scanner to image a breast, the system comprises a plastic housing and an RF coil system. The RF coil system comprises a conductor and electronics, the electronics comprising a capacitor and a blocking circuit, wherein the conductor and the electronics are disposed within the plastic housing and wherein the conductor is integrally formed with the plastic housing.

The foregoing aspect can include any one or more of the following embodiment. The conductor can be exposed within an interior of the plastic housing. The conductor can be integrally formed with the plastic housing by at least one of laser direct structuring and two-shot molding. The conductor can extend substantially along a length of the plastic housing. The conductor can extend substantially along a periphery of the plastic housing. The conductor can extend continuously around a corner and, optionally, around at least 2 corners. The conductor can be positioned on an interior of an exterior wall of the plastic housing. The plastic housing can comprise an outer enclosure and an insert disposed within and releasably coupled to the outer enclosure. The conductor can be integrally formed with the insert. The conductor can extend substantially along a length of the insert. The conductor can extend substantially along a periphery of the insert. The conductor can extend continuously around a corner and, optionally, around at least 2 corners on the insert. The conductor can be configured to face in the direction of the breast. The electronics can be coupled to and, optionally, disposed within the plastic housing.

In another aspect of the invention, a method of forming and/or assembling an MRI local coil system for use with an MRI scanner to image a breast, the method comprising providing a plastic housing, integrally forming a conductor of an RF coil system with the plastic housing, and providing electronics of the RF coil system such that the electronics are coupled to and, optionally, disposed within the plastic housing, wherein the electronics comprise a capacitor and a blocking circuit.

The foregoing aspect can include any or more of the following embodiments, the step of integrally forming the conductor can expose the conductor within an interior of the plastic housing. The step of integrally forming can be accomplished by at least one of laser direct structuring or two-shot molding. The step of integrally forming the conductor can form the conductor so as to extend substantially along a length of the plastic housing. The step of integrally forming the conductor can form the conductor so as to extend substantially along a periphery of the plastic housing. The step of integrally forming the conductor can form the conductor so as to extend continuously around a corner and, optionally, around at least 2 corners. The plastic housing can comprise an outer enclosure and an insert, the insert releasably coupled to the outer enclosure. The step of integrally forming the conductor can integrally form the conductor with the insert. The step of integrally forming the conductor can form the conductor so as to extend substantially along a length of the insert. The step of integrally forming the conductor can form the conductor so as to extend along a periphery of the insert. The step of integrally forming the conductor can form the conductor continuously around a corner and, optionally, around at least 2 corners. The step of integrally forming the conductor can form the conductor on the insert to face in the direction of the breast. The forming and/or assembling of the MRI local coil system is free and/or does not include manual tuning of the RF coil system.

BRIEF DESCRIPTION OF THE DRAWINGS

Other features and advantages of the present invention, as well as the invention itself, can be more fully understood from the following description of the various embodiments, when read together with the accompanying drawings, in which.

DETAILED DESCRIPTION OF THE INVENTION

Except as otherwise notes, the articles "a," "an," and "the" mean "one or more."

Figure 1:
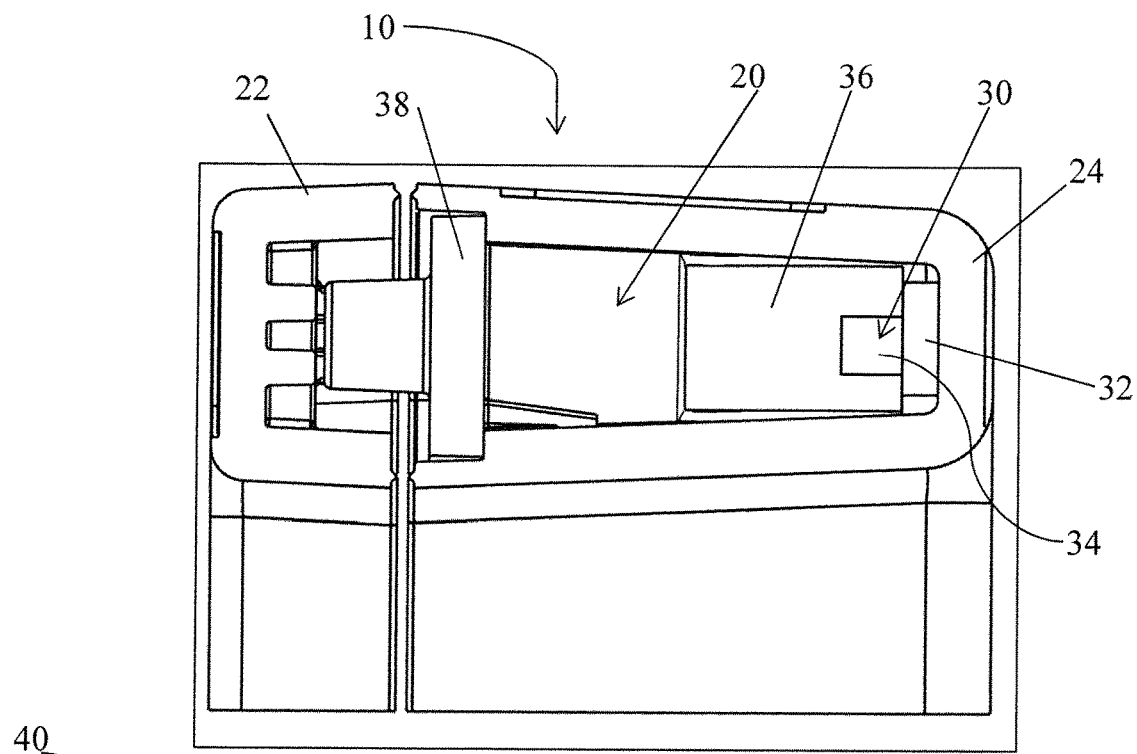
FIG. 1 is a schematic cross sectional view of a known MRI local coil design.

Referring to FIG. 1, a known MRI local coil system 10 comprises a plastic housing 20 and an RF coil system 30. The plastic housing 20 comprises a cover 22 and a case 24, coupled together. The RF coil system 30 is disposed substantially within the case 24. The RF coil system 30 comprises a conductor 32 and electronics 34. The electronics 34 may comprise a printed circuit board. The RF coil system 30 is separate from the case 24. Preloaded against the electronics 34 is a retaining foam 36 to keep the RF coil system 30 in place. A retaining cover 38 coupled to the retaining foam 36 helps to keep the retaining foam 36 in place and to couple together the cover 22 and the case 24. Alternatively, the RF coil system 30 is coupled to the case 24 via an adhesive.

Figure 2:
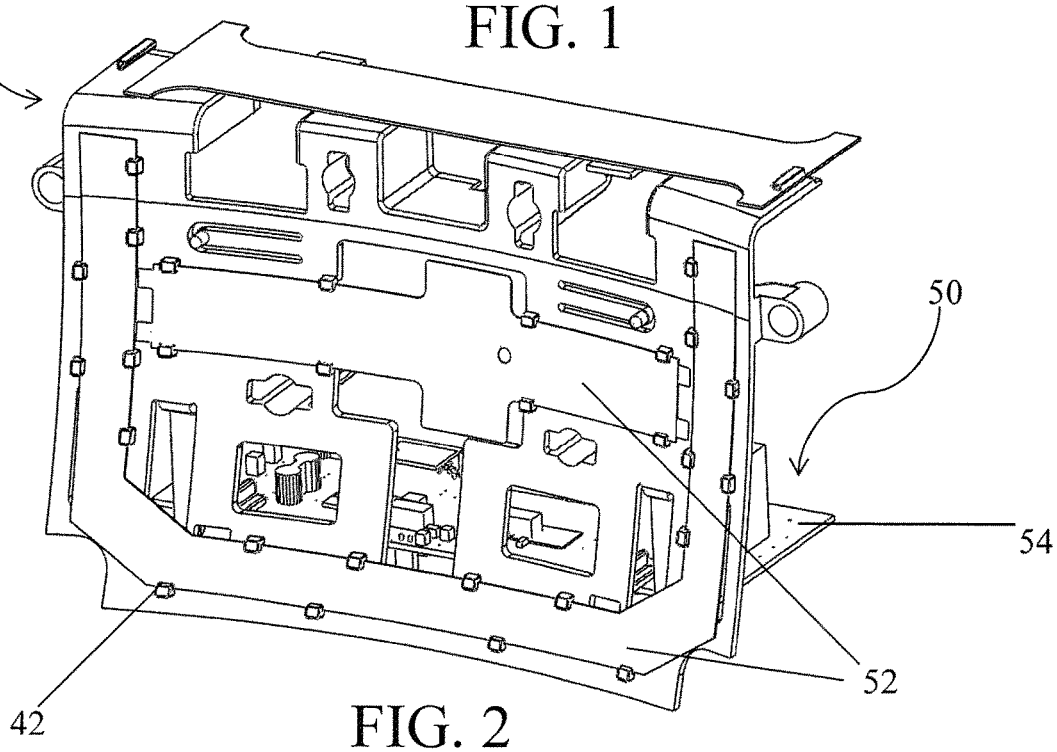
FIG. 2 is a schematic perspective view of an insert for another known MRI local coil design.

Referring to FIG. 2, alternative component of an MRI local coil system is shown. An insert 40 can be used and disposed within a plastic housing 20. The insert 40 can be made from plastic and has a curvature. Due to the curvature, at least a portion of an RF coil system 50 also has a curvature. The RF coil system 50 comprises conductors 52 and electronics 54. Conductors 52 are constructed in multiple segments to conform to the plastic housing 20. Multiple conductors 52 can be flexible to conform to the shape of the insert 40 and the electronics 54 are coupled to the insert 40 and/or a case. The insert 40 includes retention clips 42 extending from the surface of the insert 40 to retain the conductors 52. Due to the size and forces of the conductors 52, manufacturing tolerances need to be minimized so as not to compromise the quality of the RF coil system.

Figure 3:
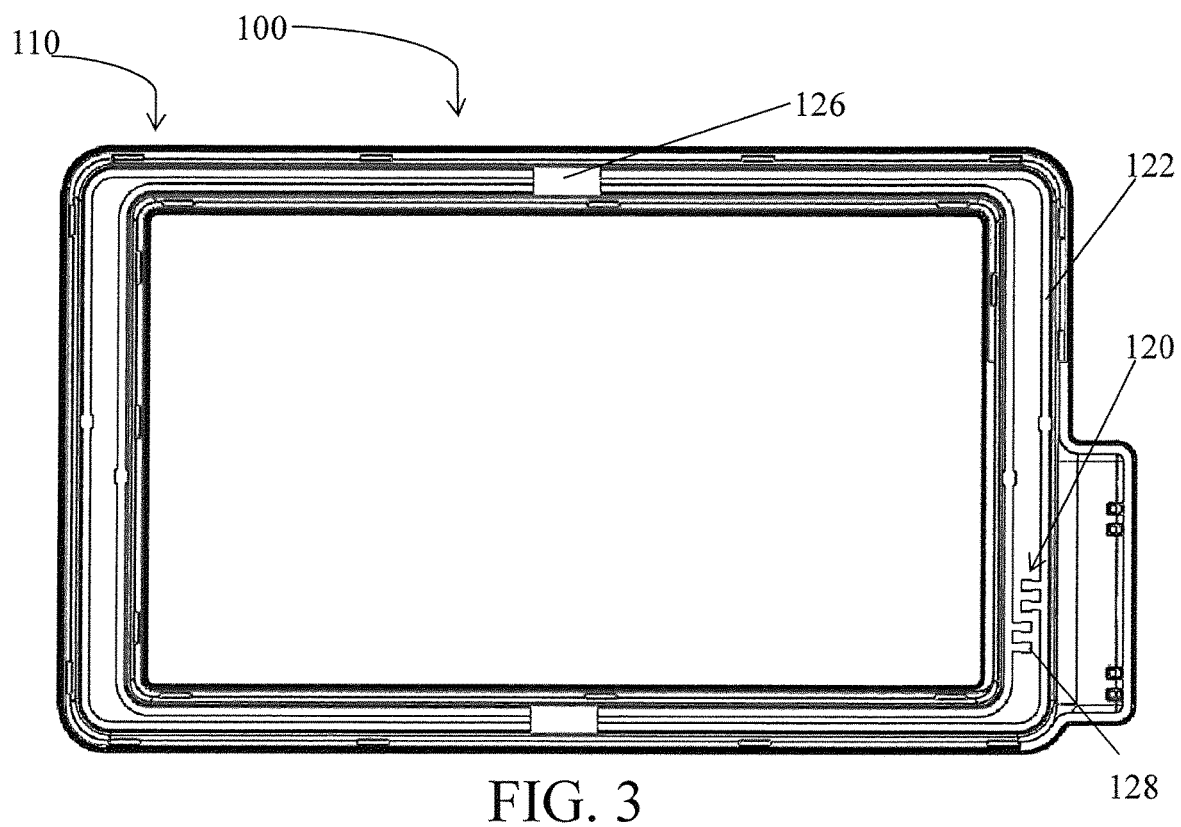
FIG. 3 is a schematic side view of a half of an MRI local coil design according to an embodiment of the invention.
Figure 4:
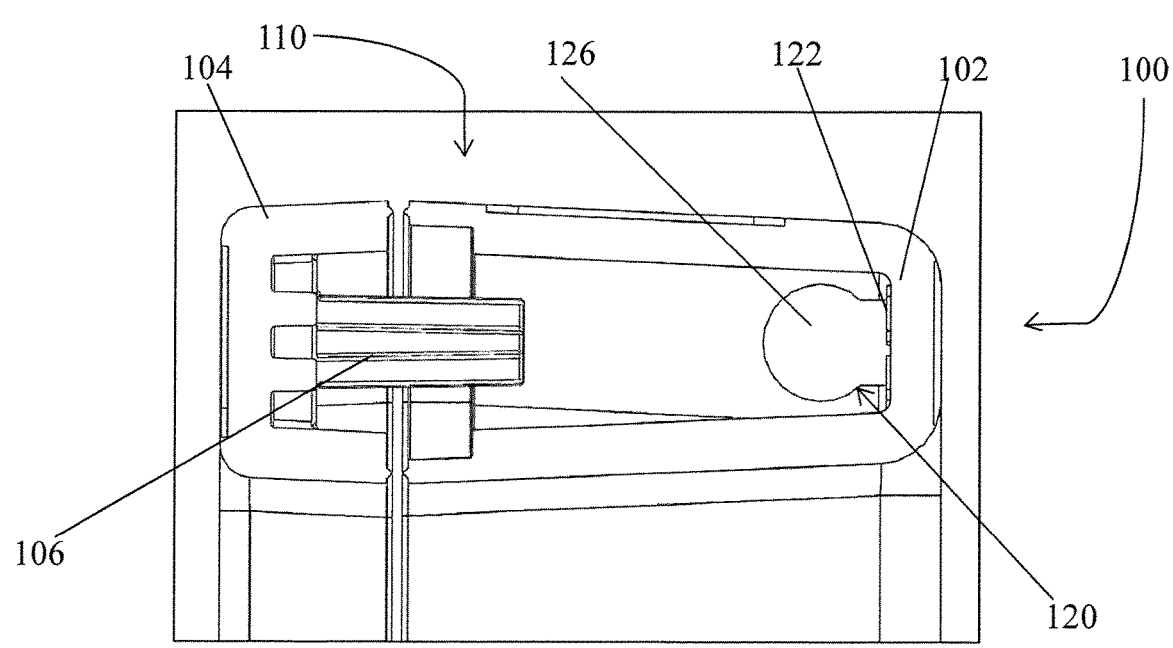
FIG. 4 is a schematic cross sectional view of an MRI local coil design in accordance with an embodiment of the invention.

FIGS. 3 and 4 depict an MRI local coil system 100. The MRI local coil system 100 comprises a plastic housing 110 and an RF coil system 120. The plastic housing 110 comprises a case 102 and a cover 104 coupled together via a retaining cover 106. The RF coil system 120 comprises a conductor 122 and electronics 124. The conductor 122 is integrally formed with the plastic housing 110 (e.g., the case 102), that is, no other structures or features, such as retention foam or retention clips, are necessary to hold the conductor 122 to the plastic housing 110. Additionally or alternatively, the RF coil system 120 may include a surface mount 126 for mounting components of the RF coil system 120, such as the conductor 122 to the plastic housing 110. The RF coil system 120 may, optionally, include pads 128 to fix components of the RF coil system 120, such as the electronics 124 to the conductor 122. The electronics 124 may include any number of components such as, but not limited to, a capacitor and a block circuit. In an embodiment, the conductor 122 comprises circuitry that receives signals in MRI. The circuitry can comprise an antenna, preamplifier, filter, printed circuit pads, lands, and vias. Additionally or alternatively, any one or more of the antenna, preamplifier, filter, printed circuit pads, lands, vias, and combinations thereof are integrally formed with the plastic housing.

In an embodiment, the conductor 122 is integrally formed with the plastic housing 110 to from a molded interconnect device (MID). The conductor 122 can be integrally formed via laser direct structuring (LDS) or two-shot molding. In an embodiment in which the conductor 122 is integrally formed via LDS, the material of the plastic housing 110 is selected such that certain properties are activated by a laser beam/chemical process so as to plate (electroplating) the surface with copper. Suitable materials include thermoplastic polymers such as Pocan® DP T 7140 LDS (available from Lanxess Corp., Leverkusen, Germany), RTP 399 X 113385 B (available from RTP Co., Winona, Minn.), and other similar materials. Integrally forming the conductor provides numerous features. As an example, fewer parts for assembly and manufacture can be used. Moreover, assembly can be more precise without requiring adhesives or preloaded foam to retain a structure against the plastic housing. The RF coil system can also have a smaller footprint and be more flexible with and conforming to designs and curves of the housing contours. With greater flexibility to housing contours, the MRI local coil system can be more easily designed to conform the MRI local coil system to patient anatomy. The conductor is the component that receives the MRI signal and, with fewer parts and more precise assembly, integrally forming the conductor can be placed that much closer to the region of interest. In an embodiment, the conductor can be placed closer to the region of interest, for example, positioned on an interior of an exterior wall of the plastic housing. In an example, the conductor can be placed up to about 1 cm closer, preferably about ¾ cm closer, and even more preferably about ½ cm to the region of interest. This facilitates and improves the signal to noise ratio (SNR) and image quality with resulting greater sensitivity. Because of fewer parts, there is greater reliability of the MRI local coil system. In addition, another advantage of assembly with fewer parts, there is reduced sensitivity to vibration as the MRI local coil system does not need separate vibration mounting of the RF coil system. That is, there are fewer parts that need to be fixed to one another and account for possible vibrations, which may lead to signal quality issues and affect SNR. Additionally, fewer parts can reduce the cost of the MRI local coil system. In an additional or alternative embodiment, each of or both of the case and cover for the plastic housing can be formed from plastic materials suitable for injection molding, further reducing cost of the MRI local coil system.

The RF coil system can be a single loop system, though the RF coil system can include any number of loops. In an embodiment, the conductor can extend substantially along a periphery of the plastic housing. Additionally or alternatively, the conductor can extend continuously around a corner and, optionally, around at least 2 corners. The conductor can be configured to face in the direction of the breast. The electronics can be coupled to and, optionally, disposed within the plastic housing.

As depicted in FIG. 3, the plastic housing includes an aperture therethrough that can, for example, be used also for biopsy procedures. Additionally or alternatively, an MRI local coil system of the present invention can be used with fixed or adjustable coils, such as that described in U.S. Pat. Nos. 7,379,769 and 7,970,452.

Figure 5A:
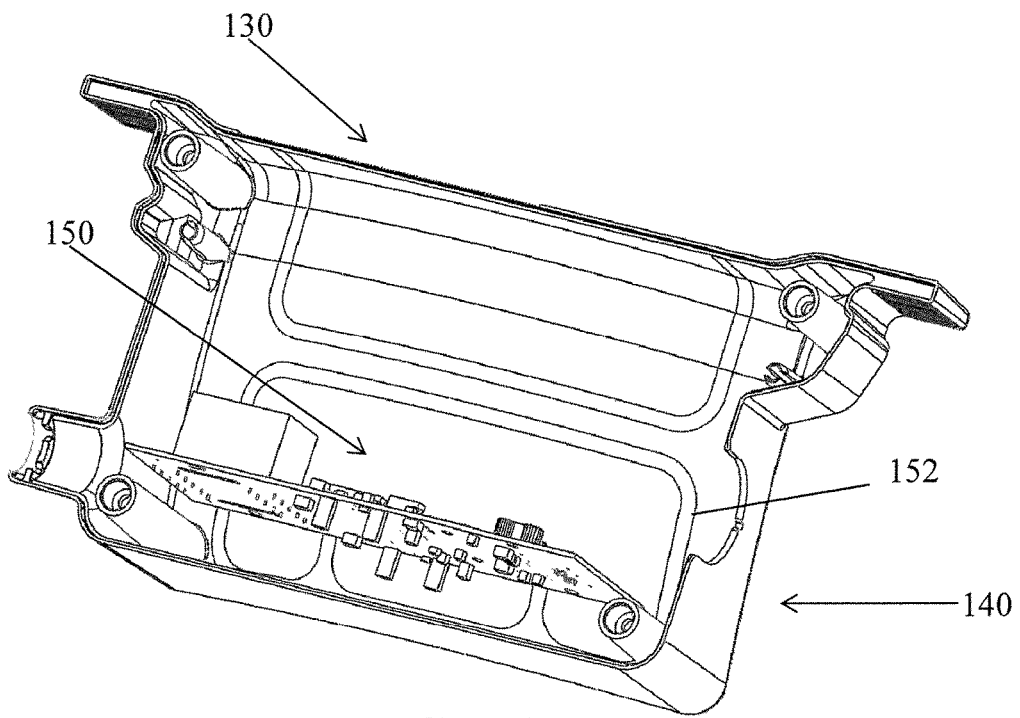
FIGS. 5A and 5B are schematic perspective and side views, respectively, of a half of an MRI local coil design according to an embodiment of the invention.
Figure 5B:
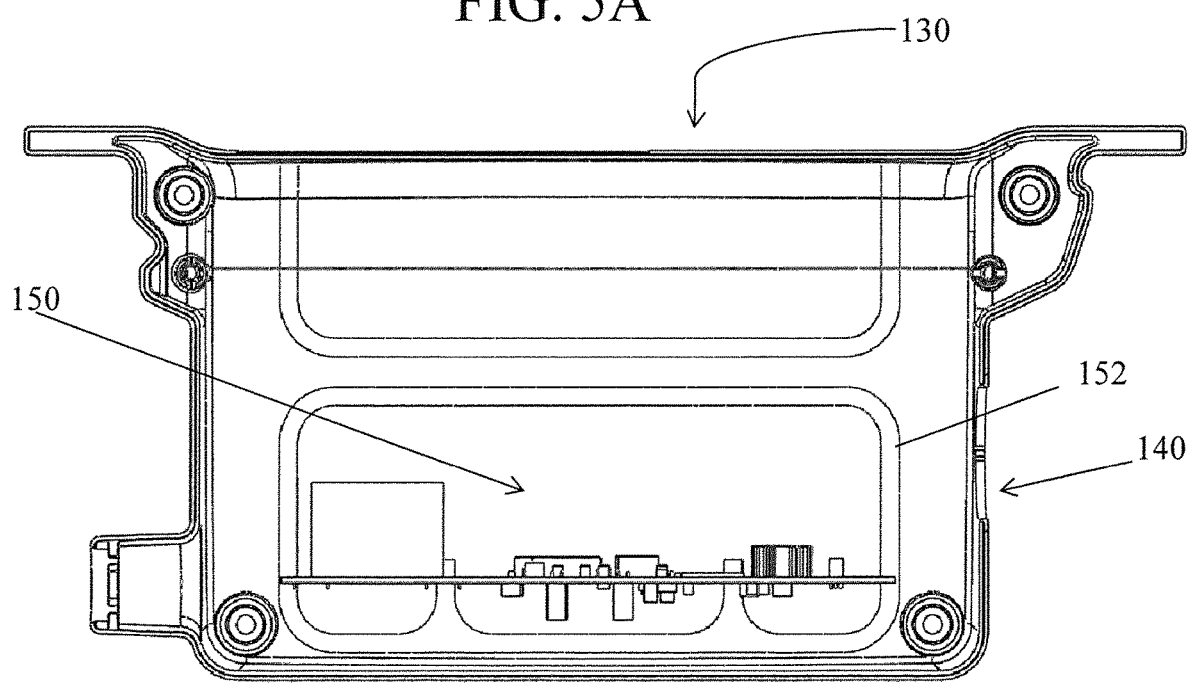

Referring now to FIGS. 5A and 5B, another embodiment of an MRI local coil system 130 comprises a plastic housing 140, optionally, without an aperture therethrough for biopsy procedures. The MRI local coil system 130 also comprises an RF coil system 150 in which a conductor 152 is integrally formed with the plastic housing 140. The conductor 152 can be directly formed on an interior of an exterior wall of the plastic housing 140 to be closer to a region of interest. In such an arrangement, an insert disposed within the plastic housing can be optional or not needed. Additionally or alternatively, the conductor 152 can be formed on more than one surface of the plastic housing 140. The conductor 152 can include more than 1 loop, such as two loops. The conductor 140 can also include more than one corner, such as two corners, or preferably up to four corners on a surface of the plastic housing 140 and, optionally, at least one corner on a first surface with another corner, in a continuous loop, on another surface orthogonal to the first surface.

Figure 6A:
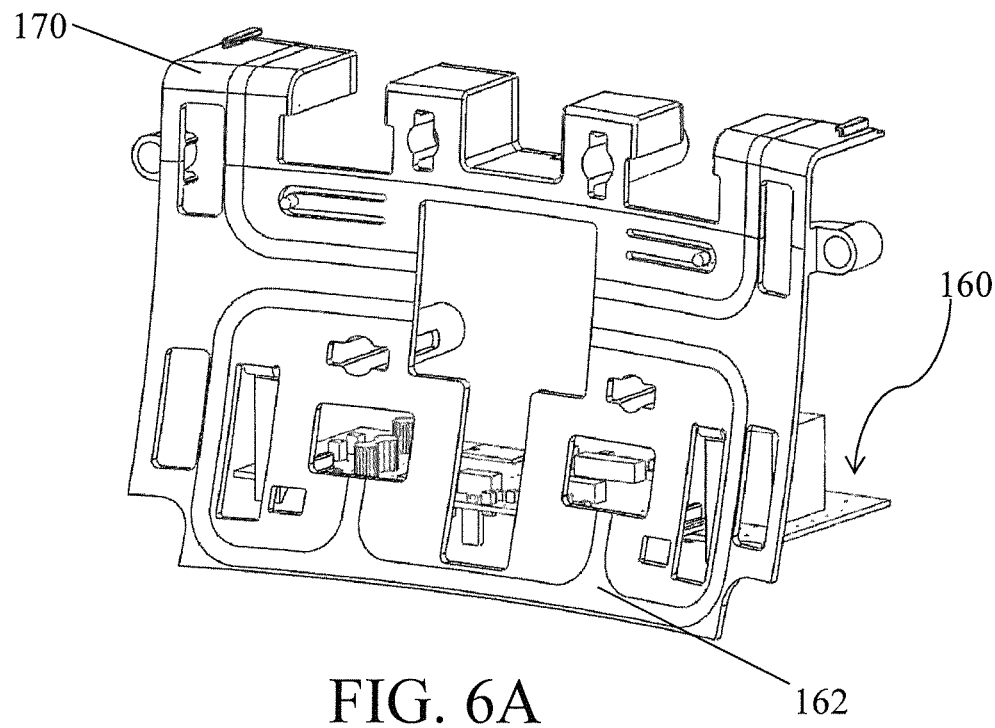
FIGS. 6A and 6B are schematic perspective and side views, respectively, of an insert of an MRI local coil design in accordance with an embodiment of the invention.
Figure 6B:
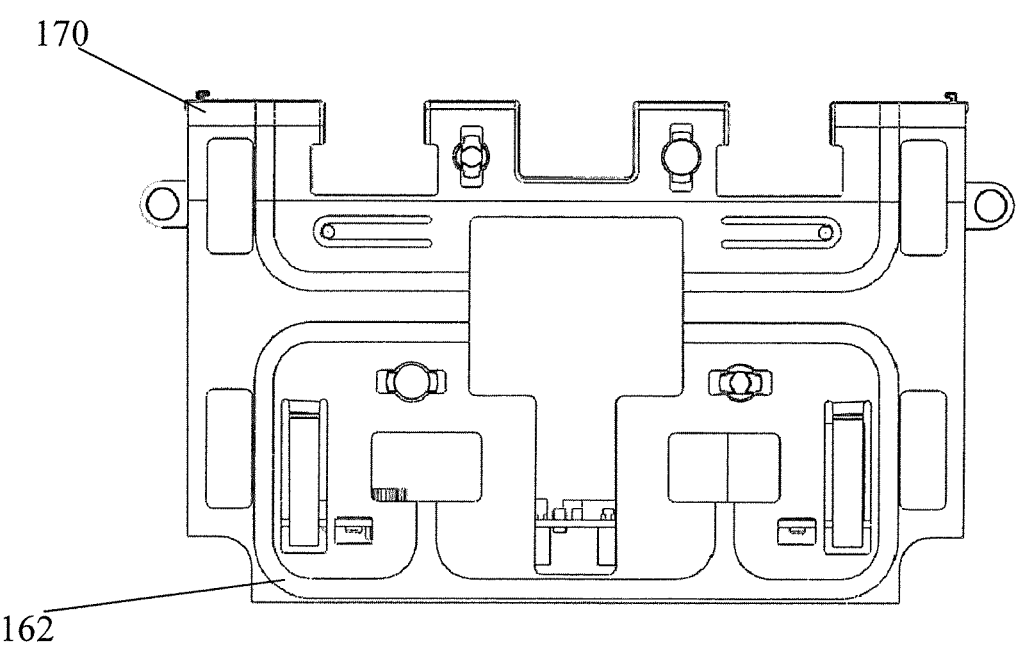

FIGS. 6A and 6B depict another embodiment of a portion of an MRI local coil system. An RF coil system 160 is coupled to at least one half of an insert 170 in which a completed insert can be placed within a plastic housing. The insert can be made of the same or similar material as previously described for a plastic housing. The conductor can be integrally formed with the insert such that the conduct faces in a direction of a region of interest. The conductor 162 can generally form a loop, though generally more loops can be utilized. The conductor 162 can be continuous along at least one corner, preferably at least two corners, and even more preferably four corners. Additionally or alternatively, the conductor 162 can span along a contour of one surface of the insert and, optionally, along a contour of two surfaces of the insert in which one surface is generally orthogonal to another surface. The conductor can extend substantially along a length of the insert. The conductor can extend substantially along a periphery of the insert. In the arrangement shown in FIGS. 6A and 6B, retention clips are not needed for the conductor 162 of the RF coil system as the conductor is formed with the plastic insert 170. Moreover, generally for all of the embodiments of the present invention, fewer parts are needed, thus providing fewer parts to assemble, more cost efficiencies as to parts, more precision of assembly, greater range of manufacturing tolerances, and greater design choices for contours of the housing, improved SNR for MRI imaging, etc.

The above described fabrication techniques of embedding a conductor described herein has additional advantages and features. In additional or alternative embodiments, the above described fabrication techniques can also include embedding non-conductive components into plastic materials. Some nonlimiting examples include embedding components such as pin diodes, ceramic capacitors, etc. Embedding conductive and non-conductive components facilitiates arbitrary three dimensional configurations to enable new designs and product solutions. Nonlimiting examples for new designs and product solutions include coil arrays, decoupling or overlapping coil elements, and/or inductive and capacitive decoupling structures. Conventional coil geometries have coil elements superimposed on one another, e.g., a loop butterfly arrangement. One disadvantage of such an arrangement, in which conductive elements cross one another, can be undesirable capacitive and inductive coupling. In an embodiment, locally increasing the spacing in the region between conductive elements due to the fabrication techniques described herein can improve performance of the coil and minimize undesirable capacitive and inductive coupling. Additionally or alternatively, the fabrication techniques described herein can automate the process of geometric decoupling or overlapping of the coil elements via process monitoring and adjustment of overlapping conductor geometry parameters and other similar methods. Moreover, various designs for inductive and capacitive decoupling structures can be enabled with the fabrication techniques due to the ability to form arbitrary three dimensional or two dimensional conductive and non-conductive component arrangements. Furthermore, the fabrication techniques facilitate automation of MRI local coil designs, for example, the coils can be automatically tuned or manual tuning can be eliminated, minimized and/or reduced. The overall shape of a MRI local coil can be customized or specified for a particular patient based on a three dimensional scan of a region of interest of the patient. The arbitrary three dimensional design of MRI local coils described herein can conform or surround any region of interest.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A magnetic resonance imaging (MRI) local coil system for use with an MRI scanner to image a breast, the MRI local coil system comprising:
   a plastic housing; and
   a radio frequency (RF) coil system comprising a conductor and electronics, the electronics comprising a capacitor and a blocking circuit, wherein
   the conductor and the electronics are disposed within the plastic housing and the conductor is integrally formed with the plastic housing by at least one of laser direct structuring and two-shot molding.

2. The MRI local coil system of claim 1, wherein the conductor is exposed within an interior of the plastic housing.

3. The MRI local coil system of claim 1, wherein the conductor extends substantially along a periphery of the plastic housing.

4. The MRI local coil system of claim 1, wherein the conductor is positioned on an interior of an exterior wall of the plastic housing.

5. The MRI local coil system of claim 1, wherein the plastic housing comprises an outer enclosure and an insert disposed within and releasably coupled to the outer enclosure.

6. The MRI local coil system of claim 5, wherein the conductor is integrally formed with the insert.

7. The MRI local coil system of claim 6, wherein the insert comprises a corner, and the conductor extends continuously around the corner of the insert.

8. The MRI local coil system of claim 1, wherein the electronics are coupled to the plastic housing.

9. The MRI local coil system of claim 1, wherein the conductor is integrally formed with the plastic housing by laser direct structuring.

10. A method of assembling a magnetic resonance imaging (MRI) local coil system for use with an MRI scanner to image a breast, the method comprising:
    integrally forming a conductor of a radio frequency (RF) coil system with a plastic housing by at least one of laser direct structuring and two-shot molding; and
    providing electronics of the RF coil system such that the electronics are coupled to and, optionally, disposed within the plastic housing, wherein
    the electronics comprise a capacitor and a blocking circuit.

11. The method of claim 10, wherein the integrally forming the conductor exposes the conductor within an interior of the plastic housing.

12. The method of claim 10, wherein the integrally forming forms the conductor to extend substantially along a periphery of the plastic housing.

13. The method of claim 10, wherein the plastic housing comprises an outer enclosure and an insert, the insert releasably coupled to the outer enclosure.

14. The method of claim 13, wherein the integrally forming the conductor forms the conductor continuously around a corner of the plastic housing.

15. The method of claim 10, further comprising excluding an operation of manually tuning the RF coil system.

16. The method of claim 11, wherein the conductor is integrally formed with the plastic housing by laser direct structuring.

* * * * *